United States Patent [19]

Boner et al.

[11] 4,195,734
[45] Apr. 1, 1980

[54] APPARATUS FOR TRANSPORTING MEDICATIONS OR THE LIKE

[76] Inventors: John O. Boner, 327 Highland Dr., Greenwood, Ind. 46142; David N. Lasiter, 7610 Singleton; Joseph H. Wilson, 5223 Turtle Creek E. Dr., both of, Indianapolis, Ind. 46227

[21] Appl. No.: 958,153

[22] Filed: Nov. 6, 1978

[51] Int. Cl.² .......................................... B65D 1/36
[52] U.S. Cl. ................................. 206/558; 206/560; 206/562; 206/564; 220/23.8; 220/345; 232/43.1; 222/559
[58] Field of Search ................ 220/23.8, 23.83, 23.86, 220/345; 206/558, 559, 561, 562, 563, 564, 565, 567; 232/43.1; 222/559, 561

[56] References Cited

U.S. PATENT DOCUMENTS

| | | | |
|---|---|---|---|
| 413,544 | 10/1889 | Peace et al. | 222/561 |
| 1,124,395 | 1/1915 | Cottrell | 220/345 |
| 1,733,565 | 10/1929 | Tobita | 206/561 |
| 2,539,326 | 1/1951 | Quitter | 206/558 |
| 3,442,378 | 5/1969 | Wolfe | 206/459 |
| 3,542,280 | 11/1970 | Crabtree | 206/558 X |
| 3,589,511 | 6/1971 | Britt | 206/558 X |
| 3,612,637 | 6/1969 | Betts | 206/561 X |
| 4,009,818 | 3/1977 | Rogers | 232/43.1 X |
| 4,078,662 | 3/1978 | Volland | 206/564 |

*Primary Examiner*—Joseph Man-Fu Moy
*Attorney, Agent, or Firm*—Woodard, Weikar, Emhardt & Naughton

[57] ABSTRACT

A tray is provided with a display area and housing area, the display area having an array of grooves for reception of hypodermic syringes, and pockets for reception of oral medications. Medication card slots are provided adjacent the grooves and pockets. A vertical wall is provided facing the needle end of syringes to prevent them from accidentally falling off the edge of the tray, and to prevent accidental brushing against the needles by the tray user or passerby. The housing portion includes a used cotton and swab receiver pocket, and a door-covered syringe receiver chamber having a sloped bottom and manually operable, when desired, to dump used syringes into a suitable final disposal container without again handling them. The tray may be made of a single piece of formable or moldable material such as plastic or metal, for example, and the door may be made of plastic or metal to best suit the circumstances.

7 Claims, 4 Drawing Figures

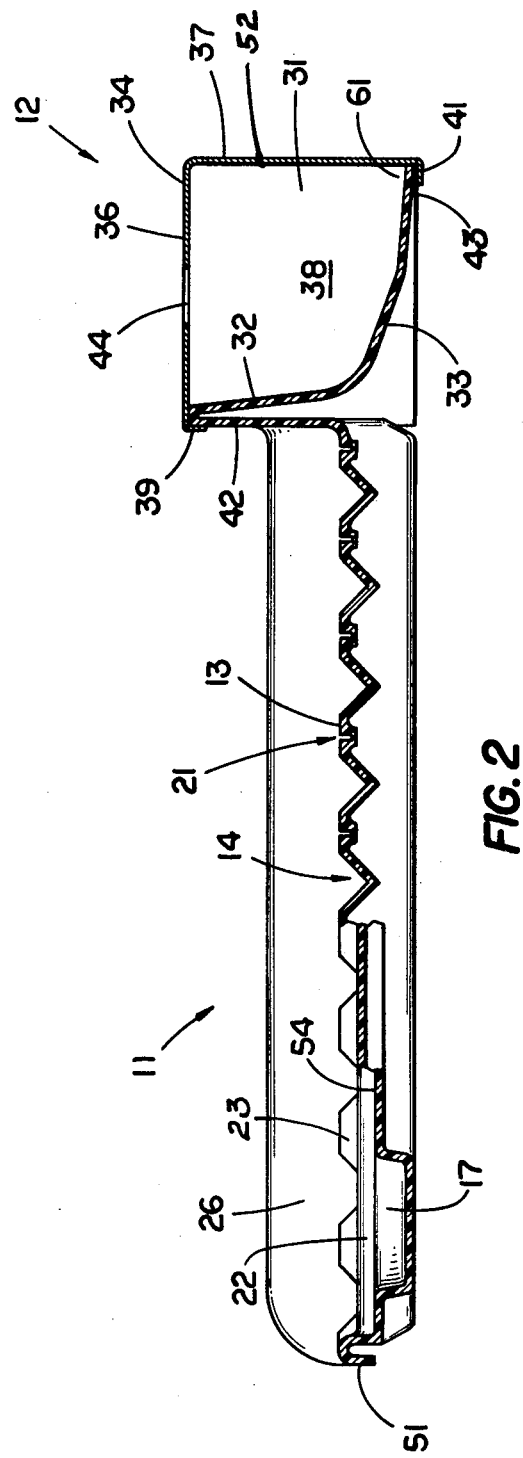
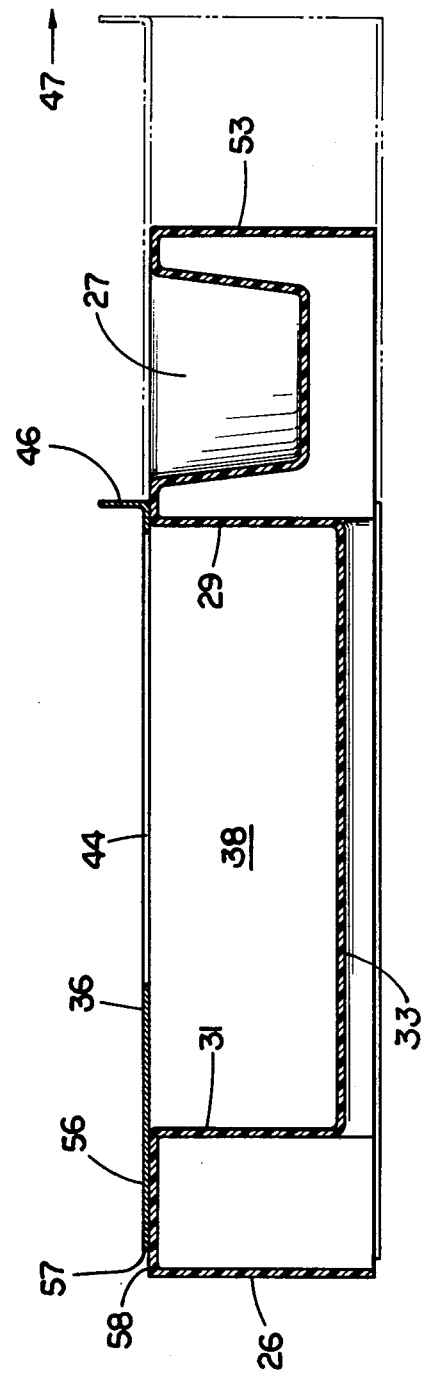

APPARATUS FOR TRANSPORTING MEDICATIONS OR THE LIKE

BACKGROUND OF THE INVENTION

1. Field of the Invention

This invention relates generally to apparatus manually transportable for administering or serving items, and more particularly to such apparatus facilitating the safe transportation and administration of medications.

2. Description of the Prior Art

In the past, needles and syringes were sterilized and re-used many times. Eventually, syringes which were made of plastic and of comparatively low cost, were inroduced and quickly accepted as a very sanitary method of handling and administering injectable materials. Because of their low cost, they were regarded as disposable. They created a new problem which was "how to dispose of the disposable".

Although machines were introduced to receive and destroy needles and syringes, there remained a problem between the point of administration of the injectable, and the point of disposition of the syringe in the machine. For example, nurses would be scratched or punctured accidentally by needles during re-capping or transporting them to the machines. Various infections resulted.

The present invention is directed to minimizing the difficulty and danger in handling needles and syringes between the time of administration of the contents, and the time of final disposition.

BRIEF SUMMARY OF THE INVENTION

Describe briefly, according to a typical embodiment of the present invention, a tray is provided with a display area and a housing area. The display area has an array of dished portions to serve as cups for receiving individual items such as medications, for example. The display area also has a corrugated portion for receiving and separating a plurality of elongated implements, such as syringes, for example. There is a housing portion which includes a chamber for reception of used syringes. This has a retainer cover closing the chamber and readily movable to an open position for dumping the chamber contents into an appropriate receptacle. The chamber cover has an opening therein adequately sized to receive a used syringe, but small enough to keep syringes from falling out when the cover is closed. A retainer wall is provided on the display area to prevent syringes form sliding off the edge of the tray.

BRIEF DESCRIPTION OF THE DRAWINGS

FIG. 2 is a section taken at line 2—2 in FIG. 1 and viewed in the direction of the arrows.

FIG. 3 is a section taken at line 3—3 in FIG. 1 and viewed in the direction of the arrows.

DETAILED DESCRIPTION

Figure 1:
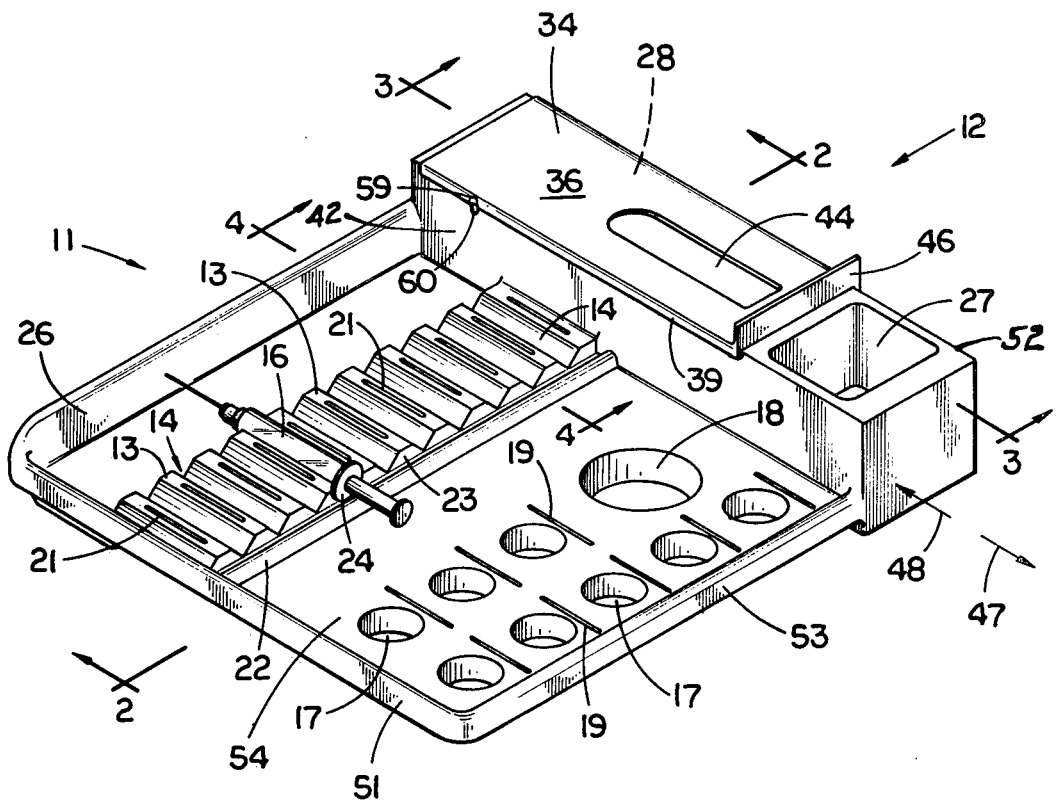
FIG. 1 is a perspective view of apparatus for transporting medications or the like, according to a typical embodiment of the present invention.
Figure 4:
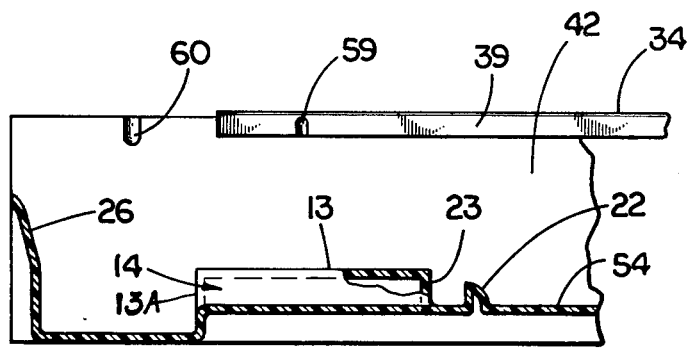
FIG. 4 is a fragmentary section taken at line 4—4 in FIG. 1 and viewed in the direction of the arrows.

Referring now to the drawings in detail, the apparatus includes a tray having a display area 11 and a housing area 12. The display area includes a number of corrugations including ribs 13 and valleys or notches or grooves 14 to receive implements, such as a syringe 16, for example. The display area also includes a plurality of depressions such as 17 which may be used to receive medications in the solid form, or medication cups or the like. A large such depression 18 may be used for cotton balls or the like. Medication card receiving slots are provided adjacent the depressions 17, and similar slots 21 are provided adjacent the grooves 14. An elongate rib 22 extends parallel to the series of parallel grooves 14, and serves to co-operate with the end walls 23 of the ribs to confine the finger flanges 24 of the syringes to limit their movement along their respective axes. In addition, an upstanding retainer wall 26 is provided parallel to the series of grooves and perpendicular to their longitudinal axes and facing the ends 13A of the ribs 14 opposite ends 23 thereof. This retainer wall serves a dual purpose of preventing accidental jarring and displacement of the syringe beyond the edge of the tray, and also prevents accidental brushing of the hand or arm against the ends of the syringes resting in the tray.

The housing area 12 includes an upwardly opening pocket 27 suitable for reception of used cotton or swabs. It also has an opening 28 which includes front wall 29 and rear wall 31 and combination side and bottom wall 32 and 33. These features are best seen in FIGS. 2 and 3. A sliding door 34 is mounted on this housing area and includes a top 36 and side wall 37 which close the opening 28 and provide a chamber 38 in the housing portion. The door also includes an upper guide flange 39 parallel to and opposite the door side wall 37, and a lower guide flange 41 at the lower marginal edge of wall 37. These flanges operate respectively on the housing sidewall 42 and the lower edge 43 of the housing wall. This door includes an elongate slot 44 in the top 36 to admit used syringes when the door is closed as shown in FIG. 1. An upstanding flange 46 is provided at the end of the door adjacent the pocket 27 and facilitates manual gripping to slide the door open in the direction of arrow 47 and closed in the direction of arrow 48. A two-thirds open position of the door is shown by dotted lines in FIG. 3.

The typical overall dimensions of the tray are 16 inches from end wall 51 to the opposite end wall 52, and 14 inches from front wall 53 to rear wall 26. The overall height of the housing portion is approximately 3 inches, while the height of the rear wall 26 is approximately 2 inches, and the height of the web 54 in the display area is about 0.75 inch.

The entire tray, except for the door, may be formed of a single piece of metal or plastic, probably about 0.0625 inch thick. It is believed that a plastic such as marketed under the trademark CYCOLAC by Borg Warner Corporation would be most satisfactory. The door may be made of plastic or metal, but stainless steel is preferable.

In FIG. 3 it will be apparent that the door substantially overlaps the end of the housing portion at 56. In this way, when a syringe is deposited in the slot 44 in the proper manner, the needle cannot possibly extend beyond the edge 57 of the door even if, by chance, it became wedged between the door and the top 58 of the housing portion adjacent the chamber 38. The preferred dimension of the slot is 1.5 inches wide by 5 inches long with a 0.75 inch radius at the end remote from the handle flange 46. The cover is preferably latched in the closed position by a friction latch, and such latch may be conveniently provided by a means of a depression or dimple 59 in the guide flange 39 received in a matching dimple 60 in the housing wall 42.

By having the sloping wall 32, 33, in the chamber 38, the syringes deposited through the slot 44 after use will immediately move downward and toward the region 61 adjacent the lower edge of the door. As the syringes accumulate, they will continue to move downward in that direction. When the chamber is full, the chamber can be readily emptied by simply sliding the door open in the direction of arrow 47 by use of the flange handle 46. The entire compartment can be readily emptied into a suitable receptacle such as the used syringe receiver of a disintegrating machine, or some other final disposal receptacle. It is unnecessary to even touch the syringes in order to accomplish this.

By use of the materials and the structural features disclosed herein, the entire unit can be machine washed and sterilized readily, whenever desired.

From the foregoing description, it should be readily recognized that the present invention not only provides and promotes safe handling of unused syringes, but also provides a safe way of handling syringes after use. There is no need to re-cap the syringe, as the entire syringe, with needle exposed, can be readily deposited in the slot 44 without fear of accidental opening of the deposit chamber.

While the invention has been illustrated and described in detail in the drawings and foregoing description, the same is to be considered as illustrative and not restrictive in character, it being understood that only the preferred embodiment has been shown and described, and that all changes and modifications that come within the spirit of the invention are desired to be protected.

What is claimed is:

1. Apparatus for transporting medications or the like and comprising:
    a tray having a display area of comparatively thin sheet material, and a housing area,
    said display area having an array of dished portions to serve as cups, and having a corrugated portion providing a plurality of parallel grooves to receive implements,
    said housing area having door support wall means therein, and
    a door on said support wall means and cooperating with said support wall means to provide a substantially closed storage chamber when said door is in a closed position, said door being movable to an open position to facilitate emptying said chamber,
    said tray having a retainer wall extending substantially perpendicular to said grooves and facing an end of said grooves,
    said chamber being elongated in a direction parallel to said grooves,
    said door having a top protion having an elongated slot therein extending parallel to said grooves,
    said chamber having a wall sloping downward and outward in a direction away from said corrugated portion of said display area, and
    said door having a sidewall portion adjoining said top portion, with said top and sidewall portions of said door closing said chamber.

2. The apparatus of claim 1 wherein:
    said door is mounted on said support wall means for sliding thereon longitudinally of said chamber from said closed position to said open position,
    said door sidewall portion cooperating with said sloping wall of said chamber when said door is in closed position, to confine the contents in said chamber by said door sidewall portion but eliminate confinement at the lower margin of said sloping wall when said door is in said open position, whereupon said sloping wall facilitates dispensing of contents of said storage chamber.

3. The apparatus of claim 2 wherein:
    said door includes an upstanding flange adjacent said slot and facilitating manipulation of said door between said closed and open positions.

4. The apparatus of claim 3 wherein:
    said manipulating flange extends parallel to said retainer wall.

5. The apparatus of claim 4 wherein:
    said tray is made of a molded impervious sheet of plastic material.

6. The apparatus of claim 5 wherein:
    said tray, including said display area and housing area, is made of a hot formed sheet of reinforced plastic material.

7. The apparatus of claim 6 wherein said material is "CYCOLAC" substantially 0.0625 inches thick.

* * * * *